US008937049B2

(12) United States Patent
Stellingwerff et al.

(10) Patent No.: US 8,937,049 B2
(45) Date of Patent: Jan. 20, 2015

(54) CARBOHYDRATE GEL (75) Inventors: Trent Stellingwerff, Le Mont-sur-Lausanne (CH); Eric Zaltas, St-saphorin (CH); Asker Jeukendrup, Birmingjam (GB)

(73) Assignee: Premier Nutrition Corporation, Emeryville, CA (US)

( * ) Notice: Subject to any disclaimer, the term of this patent is extended or adjusted under 35 U.S.C. 154(b) by 452 days.

(21) Appl. No.: 12/920,177

(22) PCT Filed: Feb. 17, 2009

(86) PCT No.: PCT/EP2009/051831
§ 371 (c)(1),
(2), (4) Date: Aug. 30, 2010

(87) PCT Pub. No.: WO2009/109460
PCT Pub. Date: Sep. 11, 2009

(65) Prior Publication Data
US 2011/0009348 A1 Jan. 13, 2011

(30) Foreign Application Priority Data
Mar. 3, 2008 (EP) .................... 08152214

(51) Int. Cl.
A61K 9/00 (2006.01)
A23L 1/09 (2006.01)
A23L 1/052 (2006.01)
A23L 1/29 (2006.01)
A23L 1/302 (2006.01)
A23L 1/304 (2006.01)
A23L 1/305 (2006.01)
A61K 9/06 (2006.01)

(52) U.S. Cl.
CPC .............. *A23L 1/095* (2013.01); *A61K 9/0056* (2013.01); *A23L 1/052* (2013.01); *A23L 1/09* (2013.01); *A23L 1/296* (2013.01); *A23L 1/302* (2013.01); *A23L 1/304* (2013.01); *A23L 1/3051* (2013.01); *A23V 2002/00* (2013.01); *A61K 9/06* (2013.01)
USPC ............................................. 514/23; 426/573

(58) Field of Classification Search
None
See application file for complete search history.

(56) References Cited

U.S. PATENT DOCUMENTS

| 3,704,168 | A | 11/1972 | Hara et al. |
| 4,310,628 | A | 1/1982 | Leiser |
| 4,322,407 | A | 3/1982 | Ko |
| 4,368,211 | A | 1/1983 | Blake et al. |
| 4,704,293 | A | 11/1987 | Moore et al. |
| 4,753,804 | A | 6/1988 | Laccheri et al. |
| 4,859,475 | A | 8/1989 | Michnowski |
| 4,871,550 | A * | 10/1989 | Millman ................ 424/601 |
| 5,108,775 | A | 4/1992 | Bousser |
| 5,270,297 | A * | 12/1993 | Paul et al. .............. 514/23 |
| 5,292,538 | A | 3/1994 | Paul et al. |
| 5,328,711 | A | 7/1994 | Coleman et al. |
| 5,626,896 | A | 5/1997 | Moore et al. |
| 5,776,887 | A | 7/1998 | Wibert et al. |
| 5,817,634 | A | 10/1998 | Olin |
| 5,908,864 | A | 6/1999 | Casey |
| 6,001,356 | A | 12/1999 | Mikecz et al. |
| 6,033,696 | A | 3/2000 | Aebischer |
| 6,039,987 | A | 3/2000 | Strahl |
| 6,207,638 | B1 | 3/2001 | Portman |
| 6,231,900 | B1 | 5/2001 | Hanke |
| 6,248,375 | B1 | 6/2001 | Gilles et al. |
| 6,440,450 | B1 | 8/2002 | Han et al. |
| 6,458,395 | B1 | 10/2002 | Emoto |
| 6,989,168 | B2 | 1/2006 | Fahey |
| 7,008,654 | B1 * | 3/2006 | Fuchs et al. .............. 426/72 |
| 2002/0015761 | A1 | 2/2002 | Prosise et al. |
| 2002/0151593 | A1 | 10/2002 | Stitley et al. |
| 2002/0174777 | A1 | 11/2002 | Guatelli |
| 2002/0187247 | A1 | 12/2002 | Saniez |
| 2003/0069757 | A1 | 4/2003 | Greenberg |
| 2003/0118712 | A1 | 6/2003 | Navarro et al. |
| 2003/0147939 | A1 | 8/2003 | King et al. |
| 2004/0013707 | A1 | 1/2004 | King et al. |
| 2004/0052852 | A1 | 3/2004 | Farber et al. |
| 2004/0086601 | A1 | 5/2004 | Ross et al. |
| 2004/0096547 | A1 | 5/2004 | Ferruzzi |
| 2004/0122097 | A1 | 6/2004 | Verlaan et al. |
| 2004/0175413 | A1 | 9/2004 | Sidebottom et al. |
| 2004/0237663 | A1 | 12/2004 | Farber et al. |
| 2005/0095271 | A1 * | 5/2005 | Mathewson .............. 424/439 |
| 2005/0137036 | A1 | 6/2005 | Smith |

(Continued)

FOREIGN PATENT DOCUMENTS

CA 2740912 A1 2/2000
CN 1391442 A 1/2003

(Continued)

OTHER PUBLICATIONS

Sawaya et al., J. Fd Techno. 1983, 18, 183-193.*
Anonymous: "Jam Dotted Shortbread Cookies" Coconut & Lime, [Online] Nov. 27, 2005, XP002496456 Retrieved from the Internet: URL:http://coconutlime.blogspot.com/2005/11/jam-dotted-shortbread-cookies.html> [retrieved on Sep. 18, 2008] "See ingredients section in recipe".

(Continued)

*Primary Examiner* — Eric Olson
(74) *Attorney, Agent, or Firm* — Thompson Coburn LLP (57) ABSTRACT

The present invention generally relates to the field of nutrition, in particular performance nutrition. In particular, the present invention relates to a novel carbohydrate gel comprising glucose and fructose in a ratio in the range of 3:1 to 1:1. The carbohydrate gel of the present invention can be used to treat or prevent problems with the gastrointestinal tract while allowing for an enhanced blood sugar maintenance and/or an increased exogenous carbohydrate oxidation.

20 Claims, 3 Drawing Sheets

(56) References Cited

U.S. PATENT DOCUMENTS

| | | |
|---|---|---|
| 2005/0215523 A1 | 9/2005 | Lai et al. |
| 2005/0226960 A1 | 10/2005 | Boice et al. |
| 2005/0260322 A1 | 11/2005 | Takaichi et al. |
| 2005/0260329 A1 | 11/2005 | Yusuf et al. |
| 2006/0024408 A1 | 2/2006 | Cicci |
| 2006/0134307 A1 | 6/2006 | Sekula et al. |
| 2006/0193949 A1 | 8/2006 | Portman |
| 2006/0216401 A1 | 9/2006 | Haisman et al. |
| 2008/0233245 A1 | 9/2008 | White et al. |
| 2009/0239803 A1 | 9/2009 | Feuvrier-roy et al. |
| 2010/0197787 A1 | 8/2010 | Doi et al. |
| 2011/0009348 A1 | 1/2011 | Jeukendrup et al. |
| 2011/0198354 A1 | 8/2011 | Frohwein |
| 2011/0236505 A1 | 9/2011 | Jeukendrup et al. |
| 2011/0311682 A1 | 12/2011 | Bacarella et al. |
| 2012/0034347 A1 | 2/2012 | Feuvrier-roy et al. |

FOREIGN PATENT DOCUMENTS

| | | | |
|---|---|---|---|
| CN | 1655692 A | 8/2005 | |
| CN | 1662147 A | 8/2005 | |
| CN | 1729860 A | 2/2006 | |
| CN | 1792257 A | 6/2006 | |
| DE | 19830768 A1 | 1/2000 | |
| EP | 259167 A2 | 3/1988 | |
| EP | 768043 A2 | 4/1997 | |
| EP | 894439 A1 | 2/1999 | |
| EP | 1302111 A1 | 4/2003 | |
| EP | 1362518 A1 | 11/2003 | |
| EP | 1506717 A1 | 2/2005 | |
| EP | 1597978 A1 | 11/2005 | |
| EP | 1629730 A1 | 3/2006 | |
| EP | 1712139 A1 | 10/2006 | |
| EP | 1762271 A2 | 3/2007 | |
| EP | 2098126 A1 | 9/2009 | |
| EP | 2098125 B1 | 10/2011 | |
| GB | 2112408 A | 7/1983 | |
| JP | 58-005376 A | 1/1983 | |
| JP | 4020250 A2 | 1/1992 | |
| JP | 53-04906 A2 | 11/1993 | |
| JP | 06-125739 A | 5/1994 | |
| JP | 2003-505099 A | 2/2003 | |
| JP | 2003-511095 A | 3/2003 | |
| JP | 2003-526354 A | 9/2003 | |
| JP | 2004-008165 A | 1/2004 | |
| JP | 2004-520846 A | 7/2004 | |
| JP | 2004-520849 A | 7/2004 | |
| JP | 2004-524040 A | 8/2004 | |
| JP | 2004-526744 A | 9/2004 | |
| JP | 2004-321140 A | 11/2004 | |
| JP | 2005-510498 A | 4/2005 | |
| JP | 2005-520534 A | 7/2005 | |
| JP | 2005-527591 A | 9/2005 | |
| JP | 2006-515510 A | 6/2006 | |
| JP | 2006-241140 A | 9/2006 | |
| JP | 2006-521106 A | 9/2006 | |
| JP | 2006-282576 A | 10/2006 | |
| JP | 2008-508891 A | 3/2008 | |
| JP | 2008-532543 A | 8/2008 | |
| RU | 2163449 C1 | 2/2001 | |
| RU | 2311798 C2 | 12/2007 | |
| SU | 1660668 A1 | 7/1991 | |
| WO | WO9112734 A1 | 9/1991 | |
| WO | WO9402127 A1 | 2/1994 | |
| WO | WO9512991 A1 | 5/1995 | |
| WO | WO 9707690 * | 3/1997 | ................ A23L 1/29 |
| WO | WO9817286 A1 | 4/1998 | |
| WO | WO9934690 A1 | 7/1999 | |
| WO | WO9938390 A1 | 8/1999 | |
| WO | WO0108505 | 2/2001 | |
| WO | WO0128360 A1 | 4/2001 | |
| WO | 0150879 | 7/2001 | |
| WO | 0150879 A1 | 7/2001 | |
| WO | WO0167889 A1 | 9/2001 | |
| WO | WO0167895 A1 | 9/2001 | |
| WO | WO02078458 A1 | 10/2002 | |
| WO | WO02078466 A1 | 10/2002 | |
| WO | WO03000068 A1 | 1/2003 | |
| WO | WO03079818 A1 | 10/2003 | |
| WO | WO2004010796 A1 | 2/2004 | |
| WO | WO2004052900 A1 | 6/2004 | |
| WO | WO2004073420 A1 | 9/2004 | |
| WO | WO2004084655 A1 | 10/2004 | |
| WO | WO2005020709 A1 | 3/2005 | |
| WO | WO2005079819 A1 | 9/2005 | |
| WO | WO2005099480 A1 | 10/2005 | |
| WO | WO2006015880 A1 | 2/2006 | |
| WO | WO2006034586 A1 | 4/2006 | |
| WO | WO2006098644 A1 | 9/2006 | |
| WO | WO2006127481 A1 | 11/2006 | |
| WO | WO2007043363 A1 | 4/2007 | |
| WO | 2007072184 | 6/2007 | |
| WO | 2007072184 A2 | 6/2007 | |
| WO | WO2008051170 A2 | 5/2008 | |
| WO | WO2008112846 A1 | 9/2008 | |
| WO | WO2008115563 A1 | 9/2008 | |
| WO | WO2009099628 A2 | 8/2009 | |
| WO | WO2009109460 A1 | 9/2009 | |
| WO | WO2009109516 A1 | 9/2009 | |
| WO | WO2012145346 A2 | 10/2012 | |

OTHER PUBLICATIONS

Anonymous: "C2 Max" Internet Article, [Online] 2006, XP002496457 Retrieved from the Internet: URL:http://www.powerbar.com/Products/PowerGel/Flavors.aspx?id=DA7E6F48-5649-4B3A-A26F-E10AAB209785> [retrieved on Sep. 17, 2008] Presented at the 2006 annual American College of Sports Medicine meeting, Denver, CO by D. Asker Jeukendrup. "see document description" &. Oct. 2007, Retrieved from the Internet; URL:http://www.powerbar.com/Products/PowerGel/flavors.aspx?id=DA7E6F48-5679-4B3A-A26F-E10AAB209785>.

Anonymous "Accelerate Accel Gel (Advanced Sports Energy Gel)" Sporty's Health. [Online] Nov. 2, 2007, pp. 1-4. XP002496458 Retrieved from the Internet: URL:///www.sportyshealth.com.au/Accelerade-Accel-Gel-Advanced-Sports-Energy-Gel-p-6456.html> [retrieved on Sep. 17, 2008] "see document description".

Anonymous; "Home made Power Gels—Energy for Less" Summitpost.org. [Online] Oct. 29, 2006, pp. 1-5, XP002496459 Retrieved from the Internet: URL:http://www.summitpost.org/article/239378/home-made-power-gels-energy-for-less.html> [retrieved on Sep. 17, 2008] "see document description".

Anonymous: "GlucoBurst Glucose Gel" Internet Article, [Online] Nov. 19, 2007, pp. 1-2, XP002496460 Retrieved from the Internet: URL:http://www.glucoburst.com/glucose-gel.aspx> [retrieved on Sep. 17, 2008] the whole document.

Roy L. P. G. Jentjens, 1 Luke Moseley, 1 Rosemary H. Waring, 2 Leslie K. Harding, 3 and Asker E. Jeukendrup: "Oxidation of combined ingestion of glucose and fructose during exercise" Journal of Applied Physiology, vol. 96, 2004, pp. 1277-1287, XP002496461 the whole document.

"Colorado Mountain Jams & Fine Wine Jellies", Plum Daisy Jams & Jellies, Mar. 14, 2009, pp. 6.

Conlee et al., "Effects of Glucose or Fructose Feeding on Glycogen Repletion in Muscle and Liver after Exercise or Fasting", Ann. Nutr. Metab. vol. 31, 1987, pp. 126-132.

Currell, "Superior Endurance Performance with Ingestion of Multiple Transportable Carbohydrates", Official Journal of the American College of Sports Medicine, 2008, pp. 275-281.

Dakui, Y. et al., "Medical Application of Fructose", Jiangsu Food and Fermentation, Dec. 30, 1984, pp. 6-12.

Fit Fuel, Feb. 2008.

"Food energy—methods of analysis and conversion factors", Food and Agriculture Organisation of the United Nations Rome, 2003.

Goldstein E. et al., "International society of sports nutrition position stand: caffeine and performance", Journal of the International Society of Sports Nutrition vol. 7, No. 5, 2010.

(56) References Cited

OTHER PUBLICATIONS

Hayman, "Implementing a Nutrition Education Program for Collegiate Female Athletes to Increase their Knowledge on the Relationship between Nutrition and Athletic Performance", Submitted to the Master of Arts in Education Program of Defiance College in partial fulfillment of the requirements for the degree of Master of Arts in Education, May 2008.
Hidemasa, et al., "Sugar and Health", Health and Science Series 8 Kansai Society Center, Jul. 1998, pp. 25-39.
"Gel-Bot", Hydrapak, http://web.archive.org/web/20110604233446/http://www.hydrapak.com/gel-bot/, Jun. 2011.
Rappaport, "Jam Dotted Shortbread Cookies", Coconut & Lime http://coconutlime.blogspot.com/2005/11/jam-dotted-shortbread-cookies.html, XP002496456, Nov. 27, 2005.
Travis, "Home Made Power Gels—Energy for Less", http://www.summitpost.org/article/239378/home-made-power-gels-energy-for-less.html, Oct. 29, 2006, XP002496459.
Jentjens, R et al., "High rates of exogenous carbohydrate oxidation from a mixture of glucose and fructose ingested during prolonged cycling exercise", British Journal of Nutrition vol. 93, 2005, pp. 485-492.
Luo, "Macrobiotics", http://web.archive.org/web/20100528155209/http://www.csustan.edu/Kinesiology/Faculty/Pingluo/DATA/Macrobiotics/Macrobiotics.html, May 28, 2010.
"Mack Cycle and Fitness", http://web.archive.org/web/20110606074642/http://www.mackcycleandfitness.com/gu1.html, (2011).
"Carbohydrates and the sweetness of honey", National Honey Board vol. (303) 776-2337 www.nhb.org, May 24, 2013, pp. 4.
Ogle, "Avoid Dizziness and Nausea While Exercising", Pilates, Aug. 17, 2006, pp. 2.
Patterson, "Carbohydrate-Gel Supplementation and Endurance Performance During Intermittent High-Intensity Shuttle Running", International Journal of Sport Nutrition and Exercise Metabolism, 2007, pp. 445-455.
"Peak Fuel", www.peakfuel.co.nz, Oct. 21, 2007.
Powerbar Energy Blasts Gel filled chews Raspberry, XP002601486, Sep. 20, 2010.
Ivy J., "Glycogen Resynthesis After Exercise: Effect of Carbohydrate Intake", Int. J. Sports Med. Vol. 19, XP008101419, Jun. 1, 1998, pp. S142-S145.
Jentjens R. et al., "Determinants of Post-Exercise Glycogen Synthesis During Short-Term", Sports Med, vol. 33, No. 2, XP008084397, 2003, pp. 117-144.
Roquette, "ROCLYS(R) and FLOLYS(R) trademarks disappear", http://www.roquette-food.com/news-2009-prebiotics-soluble-dietary-fiber-maltitol/roclysr-and-flolysr-trademarks-disappear/, Oct. 29, 2012.
Roquette, "NEOSORB(R)70/70B", http://www.roquette-pharma.com/neosorb-sorbitol-sweet-syrups-humectants-sugarless-topical-preparations/, Oct. 29, 2012.
Sawaya et al., "Chemical characterization of prickly pear pulp, Opuntia ficus-indica, and the manufacturing of prickly pear jam", J. Fd Technol. vol. 18, 1983, pp. 183-193.
"The Encyclopedia of Cooking and Food" 27, Shufuno Tomo Co. Ltd., 1996.
"Top 10 Ways to Supercharge Your Body & Nutrition Plan for Ultimate Muscle Gains", SimplyShredded.com, http://web.archive.org/web/20100806044048/http://www.simplyshredded.com/top-10-ways-to-supercharge-your-body-nutrition-plan-for-ultimate-muscle-gains.html, Aug. 6, 2010.
"Sugar", http://food.oregonstate.edu, Nov. 19, 2005.
"The Secret to Faster Energy Delivery", Nutrition IRONMAN.com, May 25, 2006, pp. 4.
XP008101524, "Muscle and liver glycogen resynthesis following oral glucose and fructose feedings in rats", Biochemistry of Exercise; vol. 13, 1983, pp. 281-285.
Wallis et al., "Oxidation of Combined Ingestion of Maltodextrins and Fructose during Exercise", Medicine & Science in Sports & Excercise, Dec. 31, 2005, pp. 426-432.
XP002496457, "POWERBAR® C2 MAX", Premium Sports Nutrition, 2006.
XP002496458, "Accelerade Accel Gel (Advanced Sports Energy Gel)", Sporty's Health, [Online] URL:http://www.sportyshealth.com.au/Accelerade-Accel-Gel-Advanced-Sports-Energy-Gelp-6456.html>, Nov. 2, 2007, pp. 1-4.
XP002496460, "GlucoBurst Glucose Gel", Internet Article, [Online] URL:http://www.glucoburst.com/glucose-gel.aspx>, Nov. 19, 2007, pp. 1-2.
Jentjens R. et al., "Oxidation of combined ingestion of glucose and fructose during exercise", J. Appl. Physiol., vol. 96, XP002496461, 2004, pp. 1277-1284.
XP002509375, "Protein-rich bar capable of complementing protein for human body", 2006:644620, Jan. 8, 2009.
Jeukendrup et al., "Exogenous carbohydrate oxidation during ultraendurance exercise", J. Appl. Physiol. vol. 100, XP002536204, 2006, pp. 1134-1141.
XP002536205, "Food Composition and Nutrition Tables", Medpharm Scientific Publisheers (CRC Press), Stuttgart, Germany 6, 2000, pp. 884-885.
XP002601486, "Free Powerbar blasts sample", Stacy's Freebies Blog, URL:http://freebies.about.com/b/2010/02121/free-powerbar-gel-blasts-sample.htm, Feb. 21, 2010.
XP002681843, "The Australian Paradox", http://www.theaustralianparadox.com.au/Fructose.php, 2012.
Jeukendrup A. et al., "Oxidation of Carbohydrate Feedings During Prolonged Exercise", Sports Med, vol. 29, No. 6, XP002681884, Jun. 29, 2000, pp. 407-424.
Boxingscene.com (www.boxingscene.com/exercise/25092.php. wayback machine cached Dec. 28, 2007).
http://web.archive.org/web/20060315052916/http:/www.powerbar.com/NutritionResource/ToolsArticles/rticlesDetails.aspx?id=16F81EF4-4426-4321-BB09-7BC2B6A2A71D dated Mar. 15, 2006, accessed on Apr. 10, 2014 using the Internet Archive Wayback Machine.
http://web.archive.org/web/20060315033409/http:/www.powerbar.com/Products/PowerGel/Flavors.aspx?id=DA7E6F48-5649-4B3A-A26F-E10AAB209785 dated Mar. 15, 2006, accessed on Apr. 10, 2014 using the Internet Archive Wayback Machine.
Boxingscene.com (www.boxingscene.com/exercise/25092.php, wayback machine cached Dec. 28, 2007).

\* cited by examiner

CARBOHYDRATE GEL

The present invention generally relates to the field of nutrition, in particular performance nutrition. In particular, the present invention relates to a novel carbohydrate gel.

It is well established that carbohydrate ingestion during exercise improves endurance performance during prolonged (>2 h) exercise, but also during shorter duration exercise (Coyle E F, *J Sports Sci* 22: 39-55, 2004; Gisolfi C V. *Med Sci Sports Exerc* 24: 679-687, 1992, Jeukendrup A E and Jentjens R. *Sports Med* 29: 407-424, 2000).

Endurance exercise, and in particular running, has been associated with gastro-intestinal (GI) disturbances which can ultimately affect performance (for reviews see: (Brouns F, et al., Int J Sports Med 8: 175-189, 1987, Gisolfi C V. News Physiol Sci 15: 114-119, 2000, Peters H P, et. Al., Gut 48: 435-439, 2001). In fact, a 30 to 50% prevalence of exercise-related adverse GI symptoms has been reported among endurance athletes.

A variety of symptoms may occur during exercise, which may be attributed to disorders of the upper (esophagus and stomach) or lower (small bowel and colon) GI tract. Upper GI symptoms include reflux, nausea, bloating, and upper abdominal cramping. Lower GI complaints comprise lower abdominal cramping, the urge to defecate, increased frequency of bowel movements, flatulence and diarrhoea. Many of these symptoms have been shown to be exacerbated with fluid intake, and specifically carbohydrate intake, which slows gastric emptying and can lead to significant GI disturbances.

In line with these negative GI issues related to a high carbohydrate intake, and given the fact that previous research has shown that a single source of carbohydrate can only be oxidized at a maximum of 1 g/min or 60 g/h (Jeukendrup A E and Jentjens R., Sports Med 29: 407-424, 2000), in 2000 the American College of Sports Medicine (ACSM) current recommendations for carbohydrate intake during exercise is 30-60 g CHO/h (American College of Sports Medicine, American Dietetic Association, and Dietitians of Canada. Med Sci Sports Exerc 32: 2130-2145, 2000).

Recently, a series of studies has shown that a combination of multiple carbohydrate sources, in the form of a sports drink can result in a higher total carbohydrate delivery during exercise than a single carbohydrate source, which results in a 30 to 50% greater efficiency of use and exogenous carbohydrate oxidation (Jentjens R L and Jeukendrup A E, Br J Nutr 93: 485-492, 2005; Jeukendrup A E. Nutrition 20: 669-677, 2004; Jeukendrup A E and Jentjens R., Sports Med 29: 407-424, 2000; Jeukendrup A E, et al., J Appl Physiol, 2005). When subjects consumed a combination of glucose and fructose this resulted in significantly greater endurance performance compared to an isocaloric amount of glucose alone (Currell K and Jeukendrup A E. Med Sci Sports Exerc 40: 275-281, 2008). In this study subjects were able to complete a 1-hour time trial, after 2 hours of moderate intensity cycling, 8% faster when consuming a combination of glucose and fructose, compared to glucose alone.

This effect was, however, only observed when the carbohydrates were consumed in large amounts and in the form of a sports drink. In order to ingest the required amounts of carbohydrates it was necessary to consume large amounts of liquids.

These controlled laboratory findings are in contrast to real-life competition, during which athletes tend to drink smaller amounts of fluid, and ingest only small amounts of carbohydrate for fear of GI upset. No studies on the tolerance of multiple carbohydrate sources in real-life situations have been conducted so far.

Further, during exercise the ingestion of large amounts of liquids and carbohydrates causes an increase in osmolarity, which causes a decrease in gastric (stomach) emptying, and thus, a decrease in fluid delivery. This decreased gastric emptying during exercise is not wanted, since this causes bloating and an uncomfortable feeling of too much liquid sloshing in the stomach.

Additionally, consuming fructose is known to be especially distressful to GI problems with athletes (Ledochowski M, et al., Scand J Gastroenterol 36: 367-371, 2001; Mitsui T, et al., J Sports Med Phys Fitness 41: 121-123, 2001). In short, the prevalence of GI disturbances is high among endurance athletes and seems to be related to CHO intake during exercise, in particular when consuming fructose alone. Consequently, based on these findings and in view of problems with the GI tract of athletes, the consumption of fructose cannot be recommended.

Based on this prior art it was the object of the present invention to provide the art with a formulation that can provide athletes very efficiently with carbohydrates and an increased rate of exogenous carbohydrate oxidation during exercise, while at the same time minimizing the risk of developing problems with the gastrointestinal tract.

The present inventors were surprised to find that they could achieve this object by a carbohydrate gel in accordance with claim 1 and by a use in accordance with claim 12.

While the subject matter of the present invention is primarily intended for athletes, it is clear, that the carbohydrate gel of the present invention can be used by anybody in need of carbohydrate supply. For example, the gel of the present invention can be very well used as transportable food for people, who do not wish to carry too heavy provisions, for example during long term trips. The gel of the present invention may equally well be used by people to provide the body with carbohydrates for example before or during an examination in school or at university.

The present inventors have investigated the gastric tolerance of a carbohydrate gel delivering a mixture of glucose and fructose at relatively high rates during a real life situation of either running or cycling outdoors.

It was found that an intake of even 90 grams of carbohydrate per hour in the form of a carbohydrate gel, as well as 30-60 g CHO/h as recommended by the ACSM, is well tolerable for the GI-tract if ingested as carbohydrate mixture comprising glucose and fructose in a ratio in the range of 3:1 to 1:1, preferably 2:1 in the form of a gel. The gel may also comprise a carbohydrate mixture with a glucose-fructose ratio in the range of 3:1-2.3:1 and/or 1.7:1 to 1:1.

It was surprisingly found that the ingestion of 90 grams/h of the above carbohydrate mixture will allow keeping the distress of the GI-tract of athletes minimal, and at about a rate of ~15% of subjects. Furthermore it was found that the minimal GI distress was not increased as compared with an intake of 60 grams of a carbohydrate mixture comprising glucose and fructose in a ratio in the range of 3:1 to 1:1, preferably 2:1 per hour.

Consequently, one embodiment of the present invention is a carbohydrate gel comprising a carbohydrate fraction comprising glucose and fructose in a ratio in the range of 3:1 to 1:1.

A carbohydrate gel is a food product in gel form, which comprises at least one carbohydrate source and preferably a multiple carbohydrate source such as the combination of glucose and fructose, or maltodextrin and fructose.

The shape of the carbohydrate gel is not essential.

For the purpose of the present invention is a gel a product that is substantially solid at ambient temperature (i.e. in the approx. range between 10 and 40° C.). Gelled products are characterized by having a relatively soft and chewy texture. Typical gelled products includes gelatine based products as well as products based on certain types of carrageenan, alginate, starches, agarose, β-glucan, gellan gum, pectin or cellulose compounds. In general can a gel be described as a colloid in which the disperse phase has combined with the dispersion medium to produce a semisolid material, e.g., a jelly. A system is gel-like at a given frequency as soon as G' (storage modulus which concerns the solid part of the material) is higher than G" (loss modulus which concerns the liquid-like response on the material).

The gel may also be based on a gel matrix comprising sheared cell wall material from ripe and soft botanical fruits. Fruits are considered ripe after a burst of ethylene production—an important plant hormone involved in ripening—took place. Often times, ripe fruits can be easily discriminated from unripe fruits by the occurrence of a change in colour, in texture and or in taste. For example, in a preferred embodiment of the present invention a fruit is to be considered ripe if its sugar content compared to its level before the ethylene burst is increased by at least 20%. Fruits are considered soft if their firmness by a pressure measurement is below 15 N/g, preferably below 10 N/g, most preferred about 2-6 N/g. Such a corresponding gel based on cell wall material of fruits is disclosed in the applicants co-pending application EP 07109854.5 which is incorporated herein in its entirety by reference.

In sports industry today it is desirable to deliver a feeling of freshness and hydration during endurance sports to the athlete, however this is problematic as ingesting water gives an uncomfortable feeling in the stomach: too much liquid sloshing in the stomach. The carbohydrate gel of the present invention achieves this object by providing hydration while avoiding an uncomfortable feeling in the stomach.

Gels are also generally very well liked by athletes, since they are easy to carry, easy to consume and—due to their moistness—easy to swallow, even during exercises.

The multiple carbohydrate source contains fructose and glucose in a digestible form. Glucose and/or fructose may be provided in the form of fructogenic and/or glucogenic carbohydrates. Fructogenic carbohydrate means a carbohydrate which upon theoretical total hydrolysis releases at least one fructose molecule. Glucogenic carbohydrate means a carbohydrate which upon theoretical total hydrolysis releases at least one glucose molecule. Consequently, a carbohydrate can be both glucogenic and fructogenic (e.g. saccharose).

Consequently, the carbohydrates may comprise or consist of monosaccharides, such as glucose or fructose as basic carbohydrate units. The monosaccharides may represent a part of disaccharides, such as sucrose, lactose, maltose or cellobiose. The monosaccharides such as glucose or fructose may also represent a part of oligosaccharides or polysaccharides. Preferred carbohydrate sources for the present invention are maltodextrins and/or dextrose.

The carbohydrate source may additionally comprise indigestible carbohydrates, in particular fibers.

The carbohydrate fraction of the gel may comprise at least 30% glucose and fructose, preferably at least 50% glucose and fructose more preferably at least at least 85% glucose and fructose. In one embodiment of the present invention the carbohydrate fraction of the gel provides at least 50%, preferably at least 70% of the energy of the gel.

The carbohydrate gel of the present invention comprises a carbohydrate fraction and, optionally, a protein fraction and/or a fat fraction.

The presence of proteins and/or fats in the carbohydrate gel of the present invention has the advantage that this way it is possible to provide the athlete with a more complete nutrition during performance. Furthermore, the presence of proteins allows producing a carbohydrate gel with a modified taste.

As protein source, any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred.

The proteins may be intact or hydrolysed or a mixture of intact and hydrolysed proteins. It may be desirable to supply partially hydrolysed proteins (degree of hydrolysis between 2 and 20%), for example for athletes believed to be at risk of developing cows' milk allergy. Additionally, in generally at least partially hydrolysed proteins are easier and faster to metabolize by the body. This is in particular true for amino acids. Consequently, it is further preferred if the carbohydrate gel of the present invention contains single amino acids, most preferred are essential amino acids. In one embodiment the carbohydrate gel of the present invention contains amino acids such as L-leucine, L-valine and/or L-isoleucine.

If the composition includes a fat source, the fat source has the advantage that for example an improved mouth feel can be achieved. Any fat source is suitable. For example animal or plant fats may be used. To increase the nutritional value, n3-unsaturated and n6-unsaturated fatty acids may be comprised by the fat source. The fat source may also contain long chain fatty acids and/or medium chain fatty acids. For example, milk fat, canola oil, corn oil and/or high-oleic acid sunflower oil may be used.

Preferably, the gel contains less than 30 g protein per 100 g gel and/or less than 1 g fat per 100 g gel.

The carbohydrate gel may also contain minerals and micronutrients such as trace elements and vitamins in accordance with the recommendations of Government bodies such as the USRDA The carbohydrate gel of the present invention may contain vitamins, such as Vitamin C, Vitamin E, Vitamin B12, Niacin, Vitamin B6, folic acid, biotin, panthotenic acid, Vitamin $B_2$ and/or Vitamin B6, preferably in amounts that correspond to at least 10% of the recommended daily dose.

The presence of vitamins may contribute to the effectiveness of the gel and may further protect the athlete. For example, the presence of vitamin C will help to protect against catching a common cold.

The gel may also comprise electrolytes and/or minerals, such as sodium, potassium, calcium, iron, magnesium or zinc.

These compounds may contribute to the taste of the gel, may be helpful to replenish the body with compounds that the person is constantly loosing due to the generation of sweat during exercise. They may also help to prevent the generation of post-exercise muscle soreness.

The carbohydrate gel of the present invention may further contain one or more compounds selected from the group consisting of aroma compounds, fiber, caffeine, conservatives, guarana, acidifying agents, binding agents, gel building material, water, fruit juice, fruits, antioxidants, colouring agents.

These agents may improve the carbohydrate gel of the present invention with respect to many properties, such as taste, consistency, colour, and stability during storage, digestibility, and many more that are known to those of skill in the art.

The energy density of the gel is not critical for its effectiveness. However, a high energy density has the advantage that less food needs to be ingested to replenish carbohydrates as fuel to the body. Consequently, high energy densities are preferred for the gel of the present invention.

One embodiment of the present invention is characterized in that the carbohydrate gel has an energy density of 600-1500 kJ/100 g, preferably 800-1300 kJ/100 g, most preferred 850-1100 kJ/100 g.

To be easily consumable—for example during a competition or in between competitions—the serving size of the gel of the present invention is preferably relatively small. Preferably, the carbohydrate gel has a serving size of 10-100 g, preferably 15-75 g, most preferred 20-50 g.

Alternatively, the gel of the present invention may also be provided as bite size gel bits or drops with a serving size between 3 and 15 g, preferably between 5 and 10 g. This way, the carbohydrate uptake can precisely be adjusted to the needs of an athlete.

Typically, a carbohydrate gel in accordance with the present invention may contain liquids, in particular water, in an amount of 20-60 g/100 g gel. Larger water amounts are possible as well. This would have the advantage that the resulting gel would be moister and consequently easier to swallow. However, at the same time, more gel would have to be consumed to ingest a certain amount of calories from carbohydrates. Similarly also less water per 100 g gel is possible as well. Gels with a very low water content would be more difficult to swallow but—at the same time—less gel would have to be eaten to ingest a certain amount of calories from carbohydrates.

The present inventors have found that a water content of 20-60 g/100 g gel represents a very good compromise.

A typical carbohydrate gel of the present invention may comprise the following percentages of daily values (DV) based on a 2000 calorie diet: Between 0 and 1% total fat, between 5 and 9% sodium, between 0.5 and 1.5% potassium, between 12 and 16% carbohydrates, including between 5 and 10% glucose and fructose, and between 10 and 14% proteins.

Additionally it may comprise between 80 and 120% DV vitamin C, between 20 and 30% DV calcium, between 25 and 35% DV iron, between 80 and 120% DV vitamin E, between 80 and 120% DV thiamin, between 80 and 120% DV riboflavin, between 80 and 120% DV niacin, between 80 and 120% DV vitamin B6, between 80 and 120% DV folate, between 80 and 120% DV vitamin B12, between 80 and 120% DV biotin, between 80 and 120% DV pantothenic acid, between 20 and 30% DV phosphorus, between 20 and 30% DV magnesium, between 25 and 35% DV zinc, between 25 and 35% copper, and between 15 and 25% DV chromium.

The carbohydrate gel of the present invention may be used for example as a food product, as a food additive or as a nutraceutical.

In a preferred embodiment of the present invention the carbohydrate gel of the present invention is used for the preparation of a food product or as a food product to provide an increased performance, in particular endurance performance.

The formulation of this carbohydrate gel of the present invention may also be used to provide an carbohydrate delivery without any increased gastrointestinal disorders and/or to treat or prevent problems with the gastrointestinal tract.

The combination of glucose and fructose in the carbohydrate gel of the present invention allows it that the high carbohydrate content of the gel of the present invention is well tolerated by the body, so that problems of the gastrointestinal tract that one would normally expect after a high level of carbohydrate intake during exercise are at least partially avoided. Also the gastrointestinal tolerance for carbohydrates, in particular for the glucose/fructose mixture of the present invention, will be increased.

The problems with the gastrointestinal tract as mentioned above are not particularly limited but are preferably selected from the group consisting of upper abdominal problems such as reflux, heartburn, bloating, upper abdominal cramps, vomiting, nausea; lower abdominal problems such as intestinal cramps, flatulence, urge to defecate, left abdominal pain, right abdominal pain, loose stool, diarrhoea; or systemic problems such as dizziness, headache, muscle cramp or urge to urinate.

For exercise in general, but in particular for competitive exercise it is essential that the body has blood sugar available for the muscles to burn at all times. In particular at the end of a race it must be avoided, or the athlete will run out of energy. The subject matter of the present invention is well suited to prevent this. According to one embodiment of the present invention the carbohydrate gel of the present invention can be used to allow for an enhanced blood sugar maintenance late in exercise.

The carbohydrate gel of the present invention cannot only secure a long lasting blood sugar maintenance, it can also be used to provide an increased exogenous carbohydrate oxidation. Increasing exogenous carbohydrate oxidation was found to be in particular increased if the carbohydrate uptake of a person is greater than 1 g/min, preferably greater than 1.1 g/min, even more preferred greater than 1.2 g/min.

Consequently, surprisingly, optimal exogenous carbohydrate oxidation is reached at a carbohydrate ingestion above the theoretical threshold once thought for carbohydrate oxidation (Jeukendrup A E and Jentjens R., Sports Med 29: 407-424, 2000).

This way, the energy delivery from carbohydrates during physical exercise can be maximised.

Further, the carbohydrate gel of the present invention may be used to provide faster energy delivery, in particular to working muscles, and/or to provide more sustained energy to muscles. Both effects will contribute to an optimal performance of an athlete.

Finally, the carbohydrate gel of the present invention may also be used to treat or prevent symptoms of fatigue and/or to improve cycling cadence, for example measured in revolutions per minute and/or to decrease ratings of perceived exertion (RPE).

The present inventors found that the above listed uses can be successfully carried out with any amounts of carbohydrates comprising glucose and fructose in a ratio of 3:1 to 1:1 to be ingested.

However, best results were obtained, when the carbohydrate gel was used in an amount that corresponds to an ingestion of at least 30 g CHO/h, preferably at least 50 g CHO/h, more preferably at least 65 g CHO/h and most preferably between 80 g CHO/h and 110 g CHO/h.

The inventors have found that the higher the amount of carbohydrates ingested per hour is, the more the exogenous carbohydrate oxidation can be increased. A maximum of exogenous carbohydrate oxidation appears to be reached when the gel of the present invention is consumed so that 100 g-150 g carbohydrates are consumed per hour, preferably 110 g-130 g carbohydrates per hour and most preferred 115 g-125 g carbohydrates per hour.

It is clear to those skilled in the art that they can freely combine all features of the present invention disclosed herein without departing from the subject matter as disclosed.

Further features and advantages of the present invention are apparent from the following Examples and Figures.

Example 1

Gel Preparation

Carbohydrate gels of the present invention can be prepared by any method known in the art.

For example, gels can be prepared by a method comprising the following three steps. Step one involves the mixing of the ingredients and adding all the ingredients to the cooker. The primary purpose of this step is to have a smooth and homogenous mass, which is partially achieved though good stirring so all ingredients are properly dissolved. Step two involves the heating of the mass to a temperature of 75° C. for at least 10 minutes. The primary purpose of step two, which is the heating process, is to have a microbiological control and to lower the viscosity of the product to facilitate the filling process. Step three is the filling process, which is the hot-filling of the gel into pouches, followed by the hot-sealing of the pouches.

A typical gel formulation may comprise:

A carbohydrate blend (maltodextrin, fructose and/or glucose), filtered water, electrolyte blend (sodium chloride, sodium citrate, potassium chloride), citric acid, natural flavours, sodium benzoate, potassium sorbate, L-leucin (170 mg/100 g), L-valin (170 mg/100 g), L-isoleucin (170 mg/100 g), Vitamin A and Vitamin C.

Example 2

The inventors have investigated the GI tolerance of CHO gels delivering a mixture of glucose and fructose in a ratio of 2:1 at a moderate and a high dose during intense running.

In a randomised cross-over design, 26 endurance trained male and 8 female runners and triathletes (37±11 yrs; 73±9 kg; 1.76±0.07 m) completed a 16 km field-based run as fast as possible on two occasions. Once they consumed gels to provide CHO at an average rate of either 1.0 g/min (MOD) and once CHO was provided at an average rate of 1.4 g/min (HIGH) with ad libitum water intake every 3.2 km.

Figure 1:
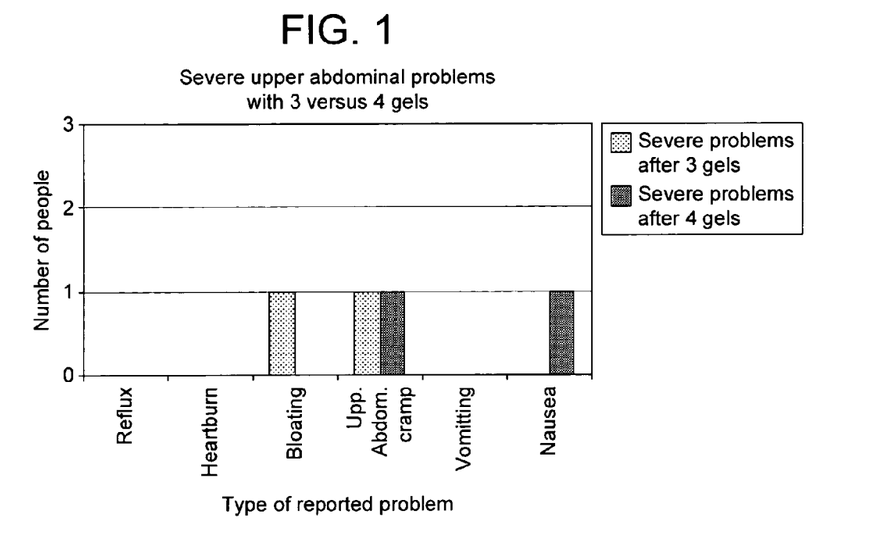
FIGS. 1-3 show the results of the study of Example 2.
Figure 2:
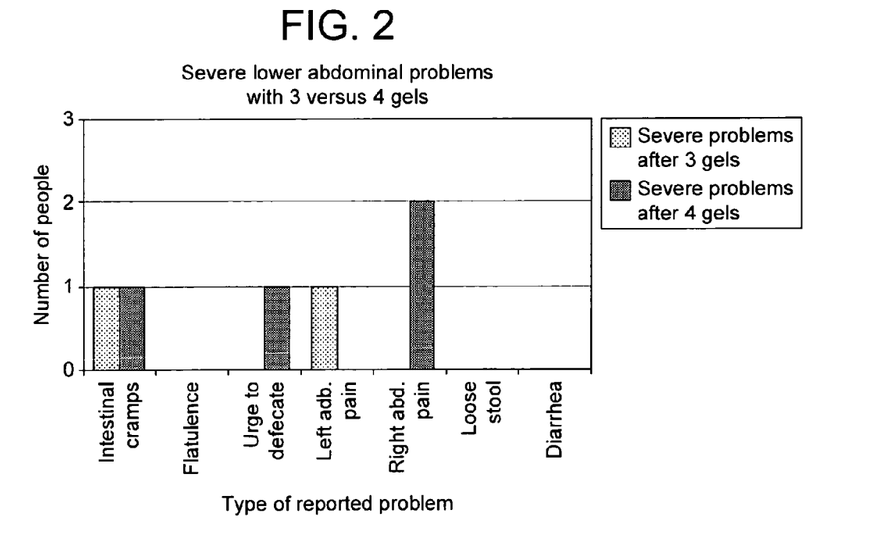
Figure 3:
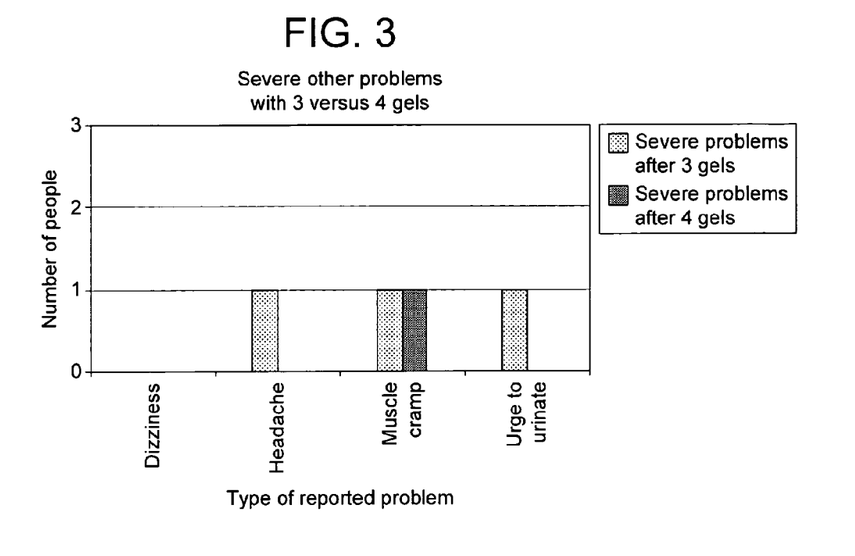

Runners completed a post-exercise questionnaire including 17 questions to assess GI comfort and tolerance on a scale from 1 to 10, from "no problem at all" to "the worst it has ever been", respectively. The results are shown in FIGS. 1-3.

For both treatments questions on GI problems were mostly scored at the low end of the scale ("no problem at all", "very minor problems"). Mean scores ranged from 1.00±0.00 (diarrhoea) to 2.12±1.90 (upper abdominal cramps). The 17 questions about symptoms were grouped into upper abdominal, lower abdominal and systemic problems. A Wilcoxon sign-rank test showed no significant treatment differences (HIGH-MOD) for upper abdominal problems (effect estimate, 0.16, se=0.08, p=0.26), for lower abdominal problems (effect estimate, 0.09, se=0.08, p=0.24) and for systemic problems (effect estimate, −0.02, se=0.14, p=0.54).

The average of the times for the first run of each participant is 1:12:08, the average of the second run was 1:12:58.

The average times of runners ingesting 3 gels is 1:13:05 whereas the time when participants ingest 4 gels is 1:13:06.

Comparing each runner for the first and the second trial 21 ran faster at the second run, 13 ran faster at their first run. 19 runners where faster when ingesting 4 gels, versus 15 where faster when ingesting three gels.

In general the average times seem not to differ very much between treatments. An indication for overall good tolerance of the given amount of gel.

Despite a high intake of CHO (glucose+fructose) in the form of gels, scores for GI problems were on average on the low end of the scale, indicating relatively good tolerance of a high CHO intake during a 16 km run.

Example 3

The inventors have investigated the effect of a high intake rate of a glucose+fructose gel versus a glucose only gel on GI tolerance.

In a double-blind, randomised, cross-over design, 34 endurance trained male and 14 female runners and triathletes (35±10 yrs; 70±9 kg; 1.75±0.09 m) completed two 16 km field based runs as fast as possible on two occasions. They received either a glucose gel (GLU) or a glucose+fructose gel (GLU/FRC) to provide CHO at a rate of 1.4 g/min with ad libitum water intake every 3.2 km. Each runner completed a post-exercise questionnaire including 17 questions to assess GI tolerance on a scale from 1 to 10 (from "no problem at all" to "the worst it has ever been").

47 runners finished both runs according to the protocol. One runner could not finish the second run because of gastrointestinal (gi) problems. She had to stop after 8 miles, but is included in the gastrointestinal results part.

Questions on complaints were predominantly scored at the low end of the scale ("no problem at all", "very minor problems") for both treatment groups. Mean scores reached from 1.00±0.0 (diarrhoea and loose stool) to 2.27±1.78 (upper abdominal cramps). The 17 questions about symptoms were grouped into upper abdominal, lower abdominal and systemic problems.

GI Problems During the Run:

During both trials the reported discomfort was in most cases at the low end of the scale (table 1).

TABLE 1

Summary statistics on treatments by question

| | | blue gel (GLU/FRC) | | | | red gel (GLU)) | | | | |
|---|---|---|---|---|---|---|---|---|---|---|
| Section | Question | n | mean | sd | min | max | n | mean | sd | min | max |
| Upper abdominal problems | Reflux | 47 | 1.51 | 1.14 | 1 | 5 | 47 | 2.04 | 1.59 | 1 | 6 |
| | Heartburn | 47 | 1.36 | 1.15 | 1 | 6 | 46 | 1.33 | 0.84 | 1 | 5 |
| | Bloating | 47 | 1.94 | 1.44 | 1 | 6 | 47 | 2.13 | 1.75 | 1 | 8 |
| | Upper abdominal cramps | 47 | 2.26 | 1.79 | 1 | 7 | 47 | 2.26 | 1.80 | 1 | 7 |
| | vomiting | 47 | 1.28 | 0.88 | 1 | 6 | 47 | 1.21 | 0.72 | 1 | 4 |
| | nausea | 47 | 2.21 | 1.68 | 1 | 7 | 47 | 2.04 | 1.81 | 1 | 8 |
| Lower | intestinal | 47 | 1.68 | 1.11 | 1 | 5 | 47 | 2.02 | 1.45 | 1 | 6 |

TABLE 1-continued

Summary statistics on treatments by question

| | | blue gel (GLU/FRC) | | | | | red gel (GLU)) | | | | |
|---|---|---|---|---|---|---|---|---|---|---|---|
| Section | Question | n | mean | sd | min | max | n | mean | sd | min | max |
| abdominal problems | cramps flatulence | 47 | 1.36 | 0.94 | 1 | 5 | 47 | 1.49 | 1.16 | 1 | 7 |
| | urge to defecate | 47 | 1.49 | 1.21 | 1 | 5 | 47 | 1.60 | 1.68 | 1 | 9 |
| | left abdominal pain | 47 | 2.15 | 1.89 | 1 | 8 | 47 | 2.11 | 1.67 | 1 | 7 |
| | right abdominal pain | 47 | 1.94 | 1.76 | 1 | 9 | 47 | 1.87 | 1.64 | 1 | 7 |
| | loose stool | 47 | 1.00 | 0.00 | 1 | 1 | 47 | 1.30 | 1.27 | 1 | 9 |
| | diarrhea | 47 | 1.00 | 0.00 | 1 | 1 | 47 | 1.02 | 0.15 | 1 | 2 |
| systemic problems | dizziness | 47 | 1.34 | 0.89 | 1 | 5 | 47 | 1.13 | 0.65 | 1 | 5 |
| | headache | 47 | 1.15 | 0.62 | 1 | 4 | 47 | 1.13 | 0.54 | 1 | 4 |
| | muscle cramp | 47 | 1.87 | 1.61 | 1 | 9 | 47 | 1.62 | 1.23 | 1 | 6 |
| | urge to urinate | 46 | 1.80 | 1.29 | 1 | 5 | 47 | 1.57 | 1.33 | 1 | 7 |

When the different treatments are compared 10 questions were scored slightly higher in the red group. For 6 questions slightly higher scores were ticked in the blue group. One was equally scored. (see table 2)

The greatest difference in scores was detected for reflux (−0.46), intestinal cramps (−0.42) and loose stool (−0.38) showing more problems with the red gel.

Calculated means over upper abdominal problems were lower for the blue gel. The same was true for lower abdominal problems. Less systemic problems were shown with the red gel.

A Wilcoxon signed rank test was applied on the mean values of each participant for each of the three sections of symptoms (for raw data see Appendix). None of them showed statistical significance.

TABLE 2

Summary statistics of treatment differences
(blue versus red gel) by question

| | | | blue - red gels | | Wilcoxon | Wilcoxon test over | |
|---|---|---|---|---|---|---|---|
| Section | Question | N | Mean | se | p values | Mean | section |
| Upper abdominal problems | Reflux | 48 | −0.46 | 0.23 | 0.024 | −0.10 | 0.76 |
| | Heartburn | 47 | 0.04 | 0.19 | 0.959 | | |
| | Bloating | 48 | −0.23 | 0.25 | 0.495 | | |
| | Upper abdominal cramps | 48 | −0.04 | 0.29 | 0.830 | | |
| | vomiting | 48 | 0.04 | 0.15 | 0.943 | | |
| | nausea | 48 | 0.15 | 0.29 | 0.505 | | |
| Lower abdominal problems | intestinal cramps | 48 | −0.42 | 0.20 | 0.041 | −0.19 | 0.22 |
| | flatulence | 48 | −0.17 | 0.16 | 0.385 | | |
| | urge to defecate | 48 | −0.21 | 0.27 | 0.339 | | |
| | left abdominal pain | 48 | −0.02 | 0.31 | 0.871 | | |
| | right abdominal pain | 48 | 0.00 | 0.31 | 0.930 | | |
| | loose stool | 48 | −0.38 | 0.20 | 0.043 | | |
| | diarrhea | 48 | −0.13 | 0.11 | 0.180 | | |
| systemic problems | dizziness | 48 | 0.15 | 0.14 | 0.277 | 0.14 | 0.15 |
| | headache | 48 | −0.04 | 0.13 | 0.915 | | |
| | muscle cramp | 48 | 0.25 | 0.20 | 0.316 | | |
| | urge to urinate | 47 | 0.21 | 0.21 | 0.271 | | |

Looking at individuals two people showed high mean values (>4) in the section of lower gi problems with the red gel. One participant noted high mean values for lower gi problems (>3) on both trials.

11 runners showed severe symptoms (>5) with the red gel, 6 runners showed severe symptoms with the blue gels and 3 runners had severe problems in both trials.

A Wilcoxon sign-rank test showed no significant treatment differences (GLU-GLU/FRC) for upper abdominal problems (effect estimate, −0.1, se=0.14, p=0.76), lower abdominal problems (effect estimate, −0.19, se=0.14, p=0.22) and systemic problems (effect estimate, 0.14, se=0.08, p=0.15). Mean run times (GLU trial: 1:14:25±7:17 h:min:sec; GLU/FRC trial: 1:14:41±7:10 h:min:sec) were not different between treatments.

Despite a high intake of CHO in the form of gels, scores for GI problems were on average at the low end of the scale, indicating relatively good tolerance of a high CHO intake during a 16 km run and there was no difference between GLU and GLU/FRC.

Example 4

Figure 4:
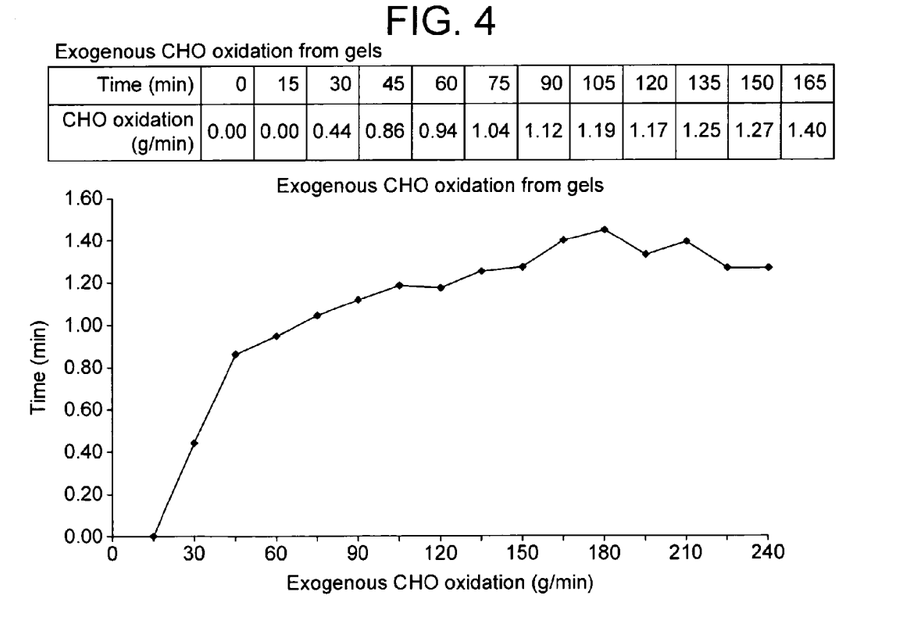
FIG. 4 shows the results of the study of Example 4.

The exogenous carbohydrate oxidation rates of a gel formulated with 2:1 glucose and fructose ratio was tested. A male cyclists rode in the lab for 3 hrs at ~60% VO2 peak followed by 1 hr of running at a similar intensity, and consumed a gel every 15 min so that the CHO consumption was 1.77 g/min. Blood and breath samples were collected throughout the 4 hrs to measure exogenous carbohydrate oxidation rates of the gel. Results are shown in FIG. 4. The peak oxidation of the multi-carbohydrate sources (2:1 glucose:fructose) gel was ~1.4 g/min, which is considerably higher than achieved with a single carbohydrate source (glucose alone at ~0.8 g/min and fructose along at ~0.4 g/min).

Example 5

The exogenous carbohydrate oxidation rates of a gel formulated with 2:1 glucose and fructose ratio was tested on 8 subjects. Further, the exogenous carbohydrate oxidation rates of a sports drink formulated with 2:1 glucose and fructose ratio was tested on 8 subjects. The test were performed as indicated in Example 4 except for this example the CHO consumption rate was 1.8 g/min.

The primary objective of this example is to measure the exogenous CHO oxidation rates (g/min) when CHO is consumed in gel form during cycling exercise, as compared to sports drink and water (using natural enrichment of $^{13}C$ carbohydrate in each specific product). This was done by the following principle:

Carbohydrates typically consist of $C^{12}$ isotopes but some carbohydrate sources have a natural abundance of $C^{13}$ isotopes. Due to this fact it is possible to determine the oxidation of exogenous carbohydrate in breath by using sources which are high in $C^{13}$ and measuring the ratio of $C^{13}/C^{12}$ in breath. Carbohydrate solutions ingested during the trial were prepared from food grade corn derived sources which have a high natural abundance of $^{13}C$.

Figure 5:
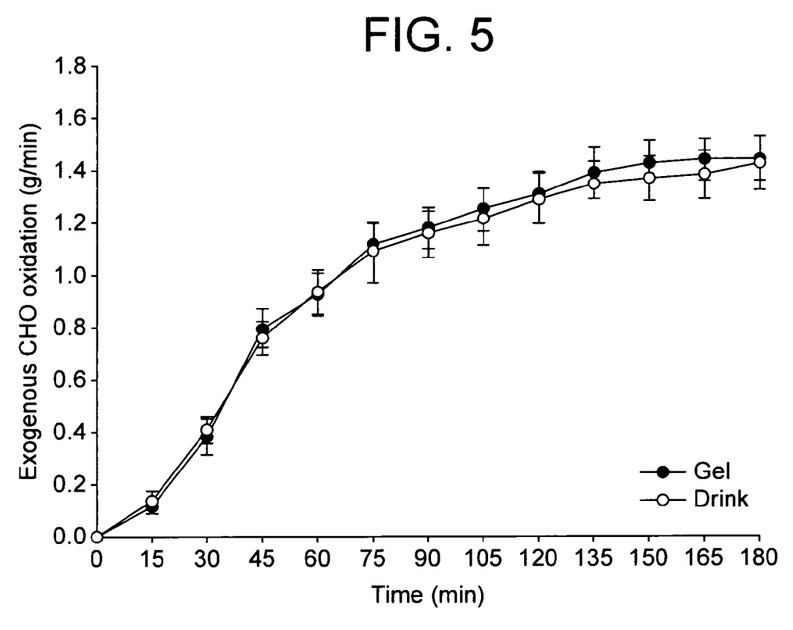
FIG. 5 shows the results of the study of Example 5.

The peak oxidation of the multi-carbohydrate sources (2:1 glucose:fructose) of the gel and of the sports drink were similar at was ~1.45 g/min. FIG. 5 shows the result of Example 5.

Example 5 shows that gels according to the present invention work just as effectively in CHO oxidation rates as a sports drink.

The invention claimed is:

1. A carbohydrate gel comprising:
   a carbohydrate fraction comprising glucose and fructose in a weight ratio in the range of 3:1 to 1:1, wherein the carbohydrate fraction of the gel comprises at least 50% glucose and fructose, and wherein glucose is present in the carbohydrate gel in the form of at least one glucose monosaccharide, at least one glucose disaccharide, and/or maltodextrin, and wherein fructose is present in the carbohydrate gel in the form of at least one fructose monosaccharide and/or at least one fructose disaccharide; and
   wherein 100 g of gel contains:
      a protein fraction present in a range of from 5 g to less than 30 g;
      less than 1 g fat;
      20-60 g water; and
      an energy density of 600-1500 kJ.

2. The carbohydrate gel of claim 1, wherein the gel further contains a vitamin selected from the group consisting of Vitamin C, Vitamin E, Vitamin $B_2$, Vitamin B6, and combinations thereof.

3. The carbohydrate gel of claim 1, wherein the gel further comprises a compound selected from the group consisting of minerals, electrolytes, and combinations thereof.

4. The carbohydrate gel of claim 1, wherein the gel further contains an amino acid selected from the group consisting of L-leucine, L-valine, L-isoleucine, and combinations thereof.

5. The carbohydrate gel of claim 1, wherein the gel has a serving size of 10-100 g.

6. The carbohydrate gel of claim 1, wherein the gel further comprises one or more compounds selected from the group consisting of aroma compounds, caffeine, ginseng, kola nut, conservatives, guarana, acidifying agents, binding agents, gel building material, water, fruit juice, fruit, antioxidants, colouring agents, and combinations thereof.

7. A method for enhancing a performance of an athlete in need of same, the method comprising:
   providing a carbohydrate gel comprising glucose and fructose in a weight ratio in the range of 3:1 to 1:1, wherein glucose is present in the carbohydrate gel in the form of at least one glucose monosaccharide, at least one glucose disaccharide, and/or maltodextrin, and wherein fructose is present in the carbohydrate gel in the form of at least one fructose monosaccharide and/or at least one fructose disaccharide, and wherein 100 g of the carbohydrate gel contains a protein fraction present in a range of from 5 g to less than 30 g, less than 1 g fat, 20-60 g water, and an energy density of 600-1500 kJ; and
   instructing the athlete to consume the carbohydrate gel.

8. A method for treating problems associated with a gastrointestinal tract in an individual in need of same, the method comprising:
   providing a carbohydrate gel comprising glucose and fructose in a weight ratio in the range of 3:1 to 1:1, wherein glucose is present in the carbohydrate gel in the form of at least one glucose monosaccharide, at least one glucose disaccharide, and/or maltodextrin, and wherein fructose is present in the carbohydrate gel in the form of at least one fructose monosaccharide and/or at least one fructose disaccharide, and wherein 100 g of the carbohydrate gel contains a protein fraction present in a range of from 5 g to less than 30 g, less than 1 g fat, 20-60 g water, and an energy density of 600-1500 kJ; and
   instructing the individual to consume the carbohydrate gel.

9. The method of claim 8, wherein the problems with the gastrointestinal tract are selected from the group consisting of reflux, heartburn, bloating, upper abdominal cramps, vomiting, nausea, intestinal cramps, flatulence, urge to defecate, left abdominal pain, right abdominal pain, loose stool, diarrhoea, dizziness, headache, muscle cramp, urge to urinate, and combinations thereof.

10. A method for providing enhanced blood sugar maintenance late in exercise in an individual in need of same, the method comprising:
    providing a carbohydrate gel comprising glucose and fructose in a weight ratio in the range of 3:1 to 1:1, wherein glucose is present in the carbohydrate gel in the form of at least one glucose monosaccharide, at least one glucose disaccharide, and/or maltodextrin, and wherein fructose is present in the carbohydrate gel in the form of at least one fructose monosaccharide and/or at least one fructose disaccharide, and wherein 100 g of the carbohydrate gel contains a protein fraction present in a range of from 5 g to less than 30 g, less than 1 g fat, 20-60 g water, and an energy density of 600-1500 kJ; and
    instructing the individual to consume the carbohydrate gel.

11. A method for providing more sustained energy to muscles of an individual in need of same, the method comprising:
    providing a carbohydrate gel comprising glucose and fructose in a weight ratio in the range of 3:1 to 1:1, wherein glucose is present in the carbohydrate gel in the form of at least one glucose monosaccharide, at least one glucose disaccharide, and/or maltodextrin, and wherein fructose is present in the carbohydrate gel in the form of at least one fructose monosaccharide and/or at least one fructose disaccharide, and wherein 100 g of the carbohydrate gel contains a protein fraction present in a range of from 5 g to less than 30 g, less than 1 g fat, 20-60 g water, and an energy density of 600-1500 kJ; and
    instructing the individual to consume the carbohydrate gel.

12. A method for treating symptoms of fatigue in an individual in need of same, the method comprising:
    providing a carbohydrate gel comprising glucose and fructose in a weight ratio in the range of 3:1 to 1:1, wherein glucose is present in the carbohydrate gel in the form of at least one glucose monosaccharide, at least one glucose disaccharide, and/or maltodextrin, and wherein fructose is present in the carbohydrate gel in the form of at least one fructose monosaccharide and/or at least one fructose disaccharid; and wherein 100 g of the carbohydrate gel contains a protein fraction present in a range of from 5 g to less than 30 g, less than 1 g fat, 20-60 g water, and an energy density of 600-1500 kJ; and instructing the individual to consume the carbohydrate gel.

13. The method of claim 12, wherein the carbohydrate gel is used in an amount that corresponds to an ingestion of at least 30 g CHO/h.

14. The carbohydrate gel of claim 1, wherein the carbohydrate gel does not contain fat.

15. The carbohydrate gel of claim 1, wherein the at least one glucose monosaccharide comprises dextrose, and the at least one glucose disaccharide comprises maltose and/or cellobiose.

16. The carbohydrate gel of claim 1, wherein the carbohydrate fraction of the gel comprises at least 70% of the energy of the carbohydrate gel.

17. The carbohydrate gel of claim 1, wherein the carbohydrate fraction of the gel comprises at least 85% glucose and fructose.

18. The carbohydrate gel of claim 1, wherein the carbohydrate fraction is present in a range of from 36 g to 48 g per 100 g of gel, and wherein glucose and fructose are present in a range of from 15 g to 30 g per 100 g of gel.

19. The carbohydrate gel of claim 1, wherein the protein fraction comprises a mixture of free amino acids.

20. The carbohydrate gel of claim 1, further defined as comprising a gel matrix comprising sheared cell wall material from at least one fruit.

* * * * *